United States Patent [19]
Down et al.

[11] Patent Number: 5,856,145
[45] Date of Patent: Jan. 5, 1999

[54] PROCESS FOR LYSING MYCOBACTERIA

[75] Inventors: James A. Down, Cary; Melinda S. Fraiser, Durham; G. Terrance Walker, Chapel Hill, all of N.C.

[73] Assignee: Becton, Dickinson and Company, Franklin Lakes, N.J.

[21] Appl. No.: 901,375

[22] Filed: Jul. 28, 1997

Related U.S. Application Data

[60] Division of Ser. No. 466,858, Jun. 6, 1995, Pat. No. 5,766,852, which is a continuation-in-part of Ser. No. 153,325, Nov. 16, 1993, abandoned.

[51] Int. Cl.⁶ .............................. C12P 19/34; C12Q 1/68
[52] U.S. Cl. ............................................. 435/91.2; 435/6
[58] Field of Search ............................. 435/6, 91.1, 91.2

[56] References Cited

U.S. PATENT DOCUMENTS 5,702,884  12/1997  Ekeze et al. ............................. 435/6
5,712,095  1/1998  Britschgi et al. ........................ 435/6

OTHER PUBLICATIONS

Savic et al. J.I.D 166:1177–1180, 1992.

Sritharan et al. Mol. Cell. Probes 5: 385–395, 1991.

*Primary Examiner*—Eggerton A. Campbell
*Attorney, Agent, or Firm*—Donna R. Fugit, Ph.D.

[57] ABSTRACT

A process for lysing Mycobacteria to liberate nucleic acids such as DNA and RNA comprises heating the Mycobacteria in an aqueous solution to lyse the Mycobacteria and release the nucleic acids, with the aqueous solution containing a chelating agent such as EDTA or EGTA in an amount effective to inhibit degradation of the released nucleic acids. Examples of Mycobacteria which can be lysed include *Mycobacterium fortuitum* and *Mycobacterium tuberculosis*. After lysis, the nucleic acid is preferably then amplified and detected. Kits useful for carrying out the present invention are also disclosed.

16 Claims, No Drawings

PROCESS FOR LYSING MYCOBACTERIA

This is a division of application Ser. No. 08/466,858, filed Jun. 6, 1995, U.S. Pat. No. 5,766,852 which is a continuation-in-part of application Ser. No. 08/153,325, filed Nov. 16, 1993, abandoned.

FIELD OF THE INVENTION

This invention relates to methods of lysing mycobacteria with heat, and methods of detecting mycobacteria employing the same.

BACKGROUND OF THE INVENTION

Mycobacteria are a large, diverse, and widely distributed family of aerobic, nonsporulating, nonmotile bacilli that have a high cell-wall lipid content and a slow growth rate. Some Mycobacteria are harmless, while others such as *M. tuberculosis* are significant pathogens. Mycobacterial species are differentiated by their growth rate, pigment production, animal virulence, and biochemical reactivity.

Many detection methods for determining the presence of pathogenic Mycobacteriaceae rely on the lysis of the organisms and amplification of nucleic acids therein. However, currently available lysis procedures are expensive, laborious, time consuming and may require caustic reagents, specialized equipment, or both. This contrasts with lysis protocols for other types of cells, which generally do not require as stringent conditions for lysis.

SUMMARY OF THE INVENTION

A first aspect of the present invention is a process for lysing Mycobacteria such as *Mycobacterium fortuitum* and *M. tuberculosis* to liberate nucleic acid therefrom. The process comprises heating the Mycobacteria in an aqueous solution for a time and to a temperature effective to lyse the Mycobacteria, with nucleic acids being liberated or released from the Mycobacteria upon lysis. The aqueous solution contains a chelating agent (e.g., EDTA, EGTA) in an amount effective to inhibit degradation of the nucleic acids released from the Mycobacteria upon lysis thereof. The heating step may be followed by amplifying and/or detecting the nucleic acid released.

A particular embodiment of the foregoing method comprises combining a biological sample suspected of containing Mycobacteria with an aqueous solution containing a chelating agent to form a lysis solution, then heating the lysis solution for a time and to a temperature effective to lyse Mycobacteria present therein. The solution contains the chelating agent in an amount sufficient to inhibit degradation of nucleic acids released from said Mycobacteria upon the lysis thereof, but insufficient to prevent subsequent amplification of a Mycobacteria nucleic acid segment in that solution. After the heating step, the step of amplifying a Mycobacteria nucleic acid segment is carried out in the lysis solution (e.g., by adding an amplification reagent to the lysis solution and reacting the amplification reagent with the Mycobacteria nucleic acid segment).

Also disclosed herein are kits useful for detecting Mycobacteria nucleic acid in a nucleic acid sample. The kits comprise a lysis solution containing a chelating agent in an amount effective to inhibit the degradation of Mycobacteria nucleic acid upon heat lysis of Mycobacteria therein, and typically also contain a nucleic acid amplification reagent capable of amplifying a Mycobacteria nucleic acid segment. The lysis solution and the amplification reagent are typically sealed in separate containers.

DETAILED DESCRIPTION OF THE INVENTION

The term "mycobacteria" as used herein has its conventional meaning in the art referring to acid-fast, non-motile, rod shaped bacteria. See generally B. Davis et al., Microbiology, 724–742 (3d Ed. 1980). All generally belong to the family Mycobacteriaceae. By way of example, the mycobacteria include, but are not limited to, *Mycobacterium africanum, M. avium, M. bovis, M. bovis*-BCG, *M. chelonae, M. fortuitum, M. gordonae, M. intracellulare, M. kansasii, M. leprae, M. microti, M. paratuberculosis, M. scrofulaceum,* and *M. tuberculosis.*

The term "nucleic acid" as used herein refers to both DNA and RNA. The present invention is particularly preferred for use with DNA as the nucleic acid.

Mycobacteria samples employed to carry out the present invention are typically obtained in the form of a sample of a biological fluid or biological tissue suspected of containing mycobacteria. Suitable biological fluids include, but are not limited to, sputum, bronchial washings, gastric washings (containing swallowed sputum), blood, milk, and lymph fluid. Suitable tissue samples include, but are not limited to, skin and other soft tissue samples (e.g., muscle, fat). As mycobacteria infect both human and animal species, the present invention is applicable to both human and veterinary diagnostic procedures, and samples may be collected from both human and animal species. For example, *M. bovis* causes tuberculosis in cattle and is transmissible to humans, and hence the present invention may be used to diagnose infection in cattle and to test cattle milk for the presence of *M. bovis* which may be transmitted to humans. Other examples are *M. avium* and *M. intracellulare*, which infect birds (e.g., chickens and pigeons) as well as swine, and hence the present invention may be used to detect such infections. Further, humans are susceptible to infection from a variety of mycobacteria, including, but not limited to, *M. tuberculosis, M. kansasii, M. avium, M. intracellulaire, M. scrofulaceum* and *M. fortuitum*, and the present invention may be used to detect such infections.

Where the sample suspected of containing the mycobacteria is a sputum sample, the sample may be digested with a liquifying agent such as N-acetyl-L-cystein (NALC) and sodium hydroxide prior to or during the heating step.

The sample suspected of containing the mycobacteria is, in general, heated for a time and to a temperature effective to lyse sufficient mycobacteria in the sample for subsequent detection, such as by means of nucleic acid amplification as described below. Such a lysis effective amount of heat is sufficient to liberate intracellular components such as DNA, RNA, and the like, but insufficient to destroy or render the desired intracellular component unsuitable for subsequent use (e.g., unsuitable for use as a substrate for DNA amplification, hybridization, and/or detection). Typically, the sample is heated for a time of 5 minutes to one hour, or more typically from 10 to 20 minutes and to a temperature of from 50° C. to 150° C., or more typically from about 70° C. to about 120° C., depending on the nature of the sample. The only limitation is that the intracellular component to be detected, typically nucleic acid, is not destroyed by the heat. Heating may be carried out by any suitable means, including, but not limited to, water baths, microwaves, ovens, flames, and the like.

Any suitable lysis solution can be used for heating the sample suspected of containing the mycobacteria. In general, the lysis solution may be water, but can also be any nucleic acid-compatible buffer such as trisbuffered saline (e.g., 50 mM Tris-HCl, 150 mM NaCl, pH 8.0), phosphate-buffered saline (e.g., 50 mM sodium phosphate, 150 mM NaCl, pH 8.0), polymerase chain reaction buffer (e.g., 10 mM tris-HCl, pH 8.8, 50 mM KCl, 1.5 mM $MgCl_2$), REACT6™ buffer solution obtained from Bethesda Research Labs (50 mM Tris-HCl, pH 7.1, 50 mM NaCl, 50 mM KCl, 6 mM $MgCl_2$), sodium phosphate solution (pH 5.0 to 12.0), TRIZMA™ 9.0 solution from Sigma Chemical Co. (trishydroxyaminomethylamine). The solution may optionally contain detergent such as 0.5% Tween 20 and 0.5% Nonidet p-40. A variety of suitable nucleic acid-compatible buffers in addition to those exemplified above are known in the art and many are described in laboratory manuals such as Molecular Cloning—A Laboratory Manual, Second Edition (J. Sambrook, E. F. Fritsch and T. Maniatis. 1989. Cold Spring Harbor Laboratory Press). The heated sample can optionally be centrifuged, making available the supernatant and pellet for subsequent use.

The lysis solution contains a chelating agent in an amount effective to combat degradation of nucleic acid after release into the lysis solution, but preferably insufficient to interfere with subsequent detection or amplification steps. The precise amount of chelating agent will depend upon the particular chelating agent employed and lysis solution, but is typically from about 1 or 10 mM up to about 50 or 100 mM. Examples of suitable chelating agents include, but are not limited to, EDTA (ethylene diamine tetraacetic acid) and EGTA (ethyleneglycol-bis($\beta$-aminoethylether)-N,N,N,N tetraacetic acid), diaminocyclohexan-tetraacetic acid (CDTA), o-phenanthroline, and salicylic acid. For EDTA, the amount included in the lysis solution is preferably about 5 mM to 15 mM, and most preferably about 10 mM. For EGTA, the amount included in the lysis solution is preferably about 1 or 2 mM to 25 or 50 mM, and most preferably from about 1 or 2 mM to 10 mM.

Once the sample is heated, subsequent use of the intracellular components can include amplification, detection, and the like. Further steps may include purification of DNA, such as by organic extraction (e.g., phenol/chloroform extraction) or solid phase adsorption onto silica surfaces such as glass or diatoms.

The process of the present invention liberates DNA and RNA from organisms in single-stranded form, enabling their direct subsequent use in an amplification or detection procedure which requires the DNA or RNA to be in single-stranded form.

Detection of mycobacteria nucleic acid (e.g., DNA or RNA) can be carried out with or without prior amplification, as discussed below. Detection may be carried out by means of Southern Blot analysis, electrophoretic gel visualization, and the like. Detection may be carried out by hybridizing a nucleic acid probe which selectively binds to mycobacteria nucleic acid thereto, which probe is labelled by conjugating a suitable detectable group thereto.

Probes can be labelled and detected by several methods. For example, probes can be radiolabelled and detected by autoradiography. Labels suitable for autoradiography include, but are not limited to, $^3H$, $^{125}I$, $^{35}S$, $^{14}C$, and $^{32}P$. Other detectable groups include ligands, fluorophores, chemiluminescent agents, electrochemical via sensors, enzymes such as horseradish peroxidase, antibodies, biotin, avidin, radionucleotides, enzyme inhibitors, co-enzymes, luciferins, paramagnetic metals, and spin labels. The choice of label dictates the manner in which the label is bound to the probe, and such binding can be carried out in accordance with known techniques.

Amplification of a selected, or target, nucleic acid sequence may be carried out by any suitable means. See generally D. Kwoh and T. Kwoh, Am. Biotechnol. Lab. 8, 14–25 (1990). Examples of suitable amplification techniques include, but are not limited to, polymerase chain reaction, ligase chain reaction, strand displacement amplification, transcription-based amplification (see D. Kwoh et al., Proc. Natl. Acad Sci. USA 86, 1173–1177 (1989)), self-sustained sequence replication (see J. Guatelli et al., Proc. Natl. Acad. Sci. USA 87, 1874–1878 (1990)), and the Q$\beta$ replicase amplification system (see P. Lizardi et al., BioTechnology 6, 1197–1202 (1988)). All such techniques generally involve at least one amplification probe, or pair of amplification probes, which serves as the amplification reagent and specifically bind to the Mycobacteria nucleic acid segment to be amplified. The amplification reagent is then reacted (e.g., cyclically reacted) with the nucleic acid segment to be amplified to effect amplification thereof.

Polymerase chain reaction (PCR) is carried out in accordance with known techniques. See, e.g., U.S. Pat. Nos. 4,683,195; 4,683,202; 4,800,159; and 4,965,188 (the disclosure of all U.S. Patent references cited herein are to be incorporated herein by reference).

Ligase chain reaction (LCR) is carried out in accordance with known techniques. See, e.g., R. Weiss, Science 254, 1292 (1991). In general, the reaction is carried out with two pairs of oligonucleotide probes: one pair binds to one strand of the sequence to be detected; the other pair binds to the other strand of the sequence to be detected. Each pair together completely overlaps the strand to which it corresponds. The reaction is carried out by, first, denaturing (e.g., separating) the strands of the sequence to be detected, then reacting the strands with the two pairs of oligonucleotide probes in the presence of a heat stable ligase so that each pair of oligonucleotide probes is ligated together, then separating the reaction product, and then cyclically repeating the process until the sequence has been amplified to the desired degree.

Strand displacement amplification (SDA) is also carried out in accordance with known techniques. See G. Walker et al., Proc. Natl. Acad. Sci. USA 89, 392–396 (1992); G. Walker et al., Nucleic Acids Res. 20, 1691–1696 (1992). SDA may be carried out with a single amplification primer or a pair of amplification primers, with exponential amplification being achieved with the latter. In general, SDA amplification primers comprise, in the 5' to 3' direction, a flanking sequence (the DNA sequence of which is noncritical), a restriction site for the restriction enzyme employed in the reaction, and an oligonucleotide sequence (e.g., an oligonucleotide probe of the present invention) which hybridizes to the target sequence to be amplified and/or detected. In addition, the step of first digesting the DNA sample to form a restriction fragment can be eliminated by exploiting the strand displacing activity of the DNA polymerase and adding a pair of "bumper" primers which bind to the substrate at a flanking position 5' to the position at which each amplification primer binds.

A kit for detecting mycobacteria nucleic acid in a nucleic acid sample contains one or more of (a) a lysis solution containing a chelating agent in a concentration as described above for obtaining a released nucleic acid sample from a mycobacteria sample, and/or (b) a hybridization solution for enabling hybridization between probes and the nucleic acid sample. Probes may be provided either suspended in the solution or provided separately in lyophilized form. One example of a suitable hybridization solution is a solution comprised of 6× SSC (0.9M sodium chloride, 0.09M sodium citrate, pH 7.0), 0.1M EDTA pH 8.0, 5× Denhardt's solution [0.1% (w/v) Ficoll Type 400, 0.1% (w/v) polyvinylpyrrolidone, 0.1% (w/v) bovine serum albumin], and 100 μg/ml sheared, denatured salmon sperm DNA, commercially available from Bethesda Research Laboratories, Gaithersburg, Md. 20877 USA under Catalog No. 5565UA. See also T. Maniatis et al., Molecular Cloning: A Laboratory Manual, 387–388 (1982) (Cold Spring Harbor Laboratory). The components of the kit are typically packaged together in a common container (e.g., a container sealed with a frangible seal). The kit typically includes instructions for carrying out the method of the present invention as described herein (e.g., as a printed instruction sheet of printed on the package or container). Additional optional components of the kit, depending on the assay format to be employed, include one or more amplification probes or a pair of amplification probes for amplifying a Mycobacteria nucleic acid segment in the sample for subsequent detection with a detection probe, one or more detection probes for detecting a mycobacteria nucleic acid segment (with or without amplification thereof), and means for carrying out a detecting step (e.g., a probe of the invention labelled with a detectable marker and optionally an enzyme substrate when the detectable marker is an enzyme).

In use, in a preferred embodiment of the invention, the biological sample suspected of containing Mycobacteria is added to the lysis solution and heated to effect lysis and release of nucleic acid. An amplification reagent is then added directly to the lysis solution and the amplification reaction carried out in the lysis solution. The amplification reagent may be in any suitable physical form, such as carried by an aqueous solution, or in dried, lyophilized, or freeze-dried form. The ability to amplify directly in the lysis solution greatly simplifies the overall detection procedure and helps reduce potential contamination of the reaction with amplicons from previous reactions. The Mycobacteria nucleic acid segment which was amplified can then be detected by any suitable means (the possibility of contamination with amplicons being less critical after the amplification step).

The present invention is explained in greater detail in the following Examples, in which "mg" means milligrams, "ml" means milliliters, "μl" means microliters, "mM" means milliMolar, "Kb" means kilobases, and temperatures are given in degrees centigrade. These Examples are illustrative of the present invention, and are not to be taken as limiting thereof.

EXAMPLE 1

Heat Lysis of Mycobacteria DNA Produces Low Molecular Weight Fragments

The purpose of this Example is to show that lysis of mycobacteria by heat produces fragmented, low molecular weight DNA. Materials employed in this Example were: Lambda phage DNA standards (obtained from Bethesda Research Laboratories): *Mycobacterium fortuitum* (Heat-inactivated, BACTEC™-cultured), approximately $10^8$ organisms/ml; 1% agarose gel; and ethidium bromide.

This example was carried out as follows: One ml of *M. fortultum* was concentrated by microcentrifugation for 5 minutes and the resulting bacterial pellet was resuspended in 100 μl of 25 mM $KPO_4$, pH 7.5 ("buffer"). This was the stock solution from which the following reactions were prepared: (1) 20 μl M. *fortuitum*+2 μl buffer; (2) 20 μl M. *fortuitum*+2 μl Lambda DNA standards; (3) 2 μl Lambda standards+20 μl buffer; (4) 2 μl Lambda standards +20 μl M. *fortuitum*; (5) 20 μl M. *fortuitum*+2 μl Lambda standards; (6) 2 μl Lambda standards+20 μl buffer.

The foregoing six reaction preparations were treated as follows: preparations 1–3 were heated for 15 minutes at, 95° C.; preparation 4 was heated 15 minutes at 95° C., cooled, and then 2 μl Lambda DNA added, and preparations 5 and 6 were not heated. The samples were then microcentrifuged briefly and analyzed on an ethidium stained 1% agarose gel. Reactions 1 and 2 showed DNA fluorescence in the size range of 2.3–0.1 kb. No discrete higher molecular weight bands were seen except for a faint band at about 9 kb. Reactions 3–6 showed discrete DNA banding at 23.1, 9.9, 6.6, 4.4, 2.3, and 2.0 Kb, as expected for the molecular weight standards.

Intact mycobacteria genomic DNA should run at about 23 kb on an agarose gel. However, when treated as described above, there was mostly low ($\leq \approx 2$ kb) molecular weight DNA released from the mycobacteria. When lysis occurred in the presence of the lambda DNA, it was also degraded, thus indicating the process of degradation was not specific for the mycobacterial DNA. Reactions in which the lambda DNA and mycobacteria were not simultaneously heated did not show degradation of the Lambda DNA, suggesting that heat and the presence of mycobacteria or its media activated a DNA degradation process which was not specific for mycobacterial DNA.

EXAMPLE 2

Effect of Chelation, Reduction and Time on Heat Lysis of Mycobacteria DNA

The purpose of this example was to determine whether chelation, reduction or time affects the degradation of mycobacterial DNA during lysis. Materials employed were as for example 1 above, also including the reducing agent dithiothreitol (DTT) and ethylenediamine tetraacetic acid (EDTA). In brief, three 1 ml aliquots of *M. fortuitum* culture were microcentrifuged for 5 minutes. Each bacterial pellet was resuspended in either: (A) 100 μl of 25 mM $KPO_4$ solution, (B) 100 μl of 25 mM $KPO_4$ solution containing 50 Mm EDTA, or (C) 100 μl of 25 mM $KPO_4$ solution containing 50 mM DTT. Twenty μl of each stock *M. fortuitum* solution was then given one of the following four treatments:

(I) heated at 95° C. for 15 minutes;

(II) 2 μl Lambda DNA were added, then the reaction was heated at at 95° C. for 15 minutes;

(III) heated at 95° C. for 15 minutes, then 2 μl Lambda DNA were added; or (IV) 2 μl Lambda DNA were added but the reaction was not heated. Control reactions containing only Lambda DNA were set up as:

(V) 2 μl Lambda DNA in 20 μl A or 20 μl B or 20 μl C and heated at 95° C. for 15 minutes. After treatment, the reaction solutions were stored overnight at 4°.

On the following day after the reactions described above, the reaction solutions were analyzed on ethidium-stained 1% agarose gels. In treatment I (heating alone), the presence of EDTA (B) resulted in DNA with a discrete molecular weight at about 20–23 kb. The other two conditions (DTT or buffer alone) produced DNA as a low molecular weight smear of size less than the 2.3 kb size marker. DTT was expected to bind free radicals, or in the alternative the sulfur therein was expected to bind metal ions, hence the lack of activity of DTT was a surprise.

Treatment II (Lambda DNA and heating) showed that the presence of EDTA conserved the Lambda DNA standards at the appropriate molecular weight while in buffer alone or in the presence of DTT the Lambda DNA markers appeared as a low molecular weight smear. In all of the other treatments, the Lambda DNA standards migrated as the appropriate sizes.

These data show that addition of 50 mM EDTA reduces the appearance of low molecular DNA from *M. fortuitum* and the apparent cleavage of Lambda DNA.

EXAMPLE 3

Titration of the Effect of Chelators on DNA Degradation During *M. fortuitum* Lysis Materials employed in this example are the same as described in Examples 1 and 2 above, including EDTA (ethylene diamine tetraacetic acid) and EGTA (ethyleneglycol-bis(β-aminoethylether)-N,N,N,N tetraacetic acid).

Three 1 ml aliquots of BACTEC™-cultured *M. fortuitum* were microcentrifuged for 5 minutes. The resulting pellets were resuspended individually with 100 microliters of 25 mM $KPO_4$ solution, pH 7.5 and then pooled. Reactions were set up as 20 μl *M. fortuitum*+2 μl chelator (either EGTA or EDTA) at one of the following tenfold serial dilutions—0.5; 0.05; 0.005; 0.0005; 0.00005 or 0.000005M. (The control consisted of adding 2 μl of 25 mM $KPO_4$). The reactions were then heated to 95° C. for 15 minutes and the debris was pelleted by microcentrifugation for one minute. Each reaction received 4 μl of type II sample buffer (described in J. Sambrook et al., Molecular Cloning: A Laboratory Manual, table 6.3 (2d Ed. 1989)(6× buffer is: 0.25% bromophenol blue; 0.25% xylene cyanol FF; 15% Ficoll (Type 400; Pharmacia) in water)) and 15 μl was analyzed by ethidium-stained 1% agarose gels. The resulting gel profiles indicated that both chelators produce inhibition of the DNA breakdown, but EGTA seemed better able to protect the genomic DNA. This suggests that the mechanism of DNA cleavage during *M. fortuitum* lysis is not magneisum-dependent, since EGTA is not a good chelator for $Mg^{2+}$.

EXAMPLE 4

Heat Lysis of *M. fortuitum* DNA in Sputum in the Presence or Absence of Chelating Agents The purpose of this Example was to determine whether lysis of *M. fortuitum* in sputum produces cleaved DNA, and whether that cleavage is stopped by chelating agents.

Materials employed in this Example are essentially the same as those described for Examples 1–3 above, and also included processed clinical sputum samples from the Veterans Administration Hospital, Durham, N.C., USA. (Accession numbers 903, 909, 904, 910, 786, 783, 987, 899, 790, 906, 901, 984, 898, 791, and 902).

One milliliter aliquots of BACTEC™-cultured *M. fortuitum* (about $10^8$ organisms/ml) were transfered into 1.5 ml SARSTEDT™ screw cap tubes and pelleted by microfugation for 5 minutes. The supernatants were discarded and about 1 ml of pooled, processed sputum was added along with about 20 mg of cotton. The samples were then mixed by hand and vortexed, then microcentrifuged for 5 minutes. The supernatants were again discarded and the pellets resuspended in 1 ml of 25 mM $KPO_4$ at pH 7.5 containing 0, 0.5, 5 or 50 mM concentrations of chelator (EDTA or EGTA). After mixing, the tubes were centrifuged again and the supernatants discarded. The tubes were then heated for 15 minutes at 95° C. About 100 μl of supernatant was aspirated from each tube and given an approximately 2 second microcentrifugation. 20 μl of those supernatants were then analyzed by electrophoresis in an ethidium-stained 1% agarose gel.

Results from these experiments were consistent with the findings reported above. During lysis of the mycobacteria, the DNA was cleaved and in the presence of either chelator the genomic-sized DNA was retained. The best results (i.e., with the most intact genomic DNA remaining) were observed with 0.5 and 5 mM EGTA.

EXAMPLE 5

Compatability of Heat Lysis in the Presence of Chelator with a DNA Amplification Reaction The purpose of this example was to demonstrate that addition of EGTA to an *M. tuberculosis* lysis reaction is compatible with the polymerase chain reaction (PCR).

Materials employed with this example were essentially as described above, except that *M. tuberculosis* was used rather than *M. fortuitum*, and PCR reagents were also used in accordance with standard techniques. In brief, 1000 *M. tuberculosis* cells were spiked into 1 ml of 25 mM $KPO_4$ at pH 7.5 and heated for 15 minutes at 95° C. 50 μl reactions were set up, to which were added 1 μl of 0.5, 0.05, 0.005, 0.0005 Molar EGTA solution or $H_2O$. Then, 50 μl of PCR buffer containing primers for the IS6110 target segment (see D. Thierry et al., IS6110, an IS-like element of Mycobacterium tuberculosis complex, *Nucleic Acids Resl*. 18, 188 (1990)) was added and PCR was carried out in accordance with standard procedures.

It was found that 10 mM EGTA inhibited the PCR reaction slightly, but other concentrations were not inhibitory. A 1 mM concentration, which did not inhibit amplification, is consistent with the concentration observed to preserve intact DNA in Example 4 above. Therefore, lysis of *M. tuberculosis* in the presence of EGTA releases intact, genomic-sized DNA, and at concentrations of EGTA below about 10 mM will not appreciably inhibit the PCR amplification.

The foregoing examples are illustrative of the present invention, and are not to be construed as limiting thereof. The invention is defined by the following claims, with equivalents of the claims to be included therein.

That which is claimed is:

1. A process for amplifying a Mycobacteria nucleic acid segment in a sample suspected of containing Mycobacteria, comprising:
    combining said sample with a lysis solution consisting essentially of less than about 10 mM EGTA in water or a nucleic acid-compatible buffer;
    heating said lysis solution for a time and to a temperature effective to lyse Mycobacteria present therein; and
    amplifying the Mycobacteria nucleic acid segment in a DNA amplification reaction in said lysis solution.

2. A process according to claim 1, wherein said amplifying step is carried out by adding an amplification reagent to said lysis solution, and reacting said amplification reagent with said Mycobacteria nucleic acid segment.

3. A process according to claim 2, wherein said amplification reagent is in dried, lyophilized or freeze-dried form.

4. A process according to claim 2, wherein said amplification reagent comprises an aqueous solution.

5. A process according to claim 1, wherein said amplification reagent is selected from the group consisting of polymerase chain reaction, ligase chain reaction, strand displacement amplification, transcription-based amplification, self-sustained sequence replication, and Qβ replicase amplification reagents.

6. A process according to claim 5, wherein said amplification reagent is a polymerase chain reaction amplification reagent.

7. A process according to claim 1, wherein said amplifying step is followed by the step of detecting said Mycobacteria nucleic acid segment.

8. A process according to claim 1, wherein said EGTA is included in said lysis solution in an amount of from 0.5–5 mM.

9. A kit useful for amplifying Mycobacteria nucleic acid in a, comprising:
   (a) a lysis solution consisting essentially of less than 10 mM EGTA in water or a nucleic acid-compatible buffer; and
   (b) a nucleic acid amplification reagent.

10. A kit according to claim 9, wherein said lysis solution consists essentially of 0.5–5 mM EGTA in water or a nucleic acid-compatible buffer.

11. A kit according to claim 9, wherein said amplification reagent is in dried, lyophilized or freeze-dried form.

12. A kit according to claim 9, wherein said amplification reagent comprises an aqueous solution.

13. A kit according to claim 9, wherein said amplification reagent is selected from the group consisting of polymerase chain reaction, ligase chain reaction, strand displacement amplification, transcription-based amplification, self-sustained sequence replication, and Qβ replicase amplification reagents.

14. A kit according to claim 9, wherein said amplification reagent is a polymerase chain reaction amplification reagent.

15. The process of claim 1 wherein the buffer is selected from the group consisting of TRIS-buffered saline, phosphate-buffered saline, polymerase chain reaction buffer, REACT6 buffer, sodium phosphate solution TRIZMA and potassium phosphate.

16. The kit of claim 9 wherein the buffer is selected from the group consisting of TRIS-buffered saline, phosphate-buffered saline, polymerase chain reaction buffer, REACT6 buffer, sodium phosphate solution TRIZMA and potassium phosphate.

* * * * *